(12) United States Patent
Hendriks et al.

(10) Patent No.: US 6,617,443 B2
(45) Date of Patent: Sep. 9, 2003

(54) METHOD FOR REMOVING ENDOTOXINS

(75) Inventors: Robertus Hendriks, Heidelberg (DE); Maria Wehsling, Darmstadt (DE); Andrea Lantos, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/220,763

(22) PCT Filed: Feb. 14, 2001

(86) PCT No.: PCT/EP01/01610

§ 371 (c)(1),
(2), (4) Date: Sep. 5, 2002

(87) PCT Pub. No.: WO01/66718

PCT Pub. Date: Sep. 13, 2001

(65) Prior Publication Data

US 2003/0068810 A1 Apr. 10, 2003

(30) Foreign Application Priority Data

Mar. 6, 2000 (DE) .......................... 100 10 342

(51) Int. Cl.$^7$ ................................ C07H 21/04
(52) U.S. Cl. ................. 536/25.41; 435/320.1
(58) Field of Search ............... 536/25.41; 435/320.1

(56) References Cited

U.S. PATENT DOCUMENTS 5,837,520 A 11/1998 Shabram et al.
2003/0032092 A1 * 2/2003 Blanche et al.

FOREIGN PATENT DOCUMENTS

WO  WO 99 63076 A  12/1999

* cited by examiner

*Primary Examiner*—James Ketter
(74) *Attorney, Agent, or Firm*—Millen, White, Zelano & Branigan, P.C.

(57) ABSTRACT

The invention relates to a method for removing endotoxins from nucleic acids. The endotoxins are removed by pre-incubating the nucleic acids in a salt-free detergent solution and subsequent anion exchange chromatography on a tentacle anion exchanger.

20 Claims, 1 Drawing Sheet

METHOD FOR REMOVING ENDOTOXINS

Figure 1:
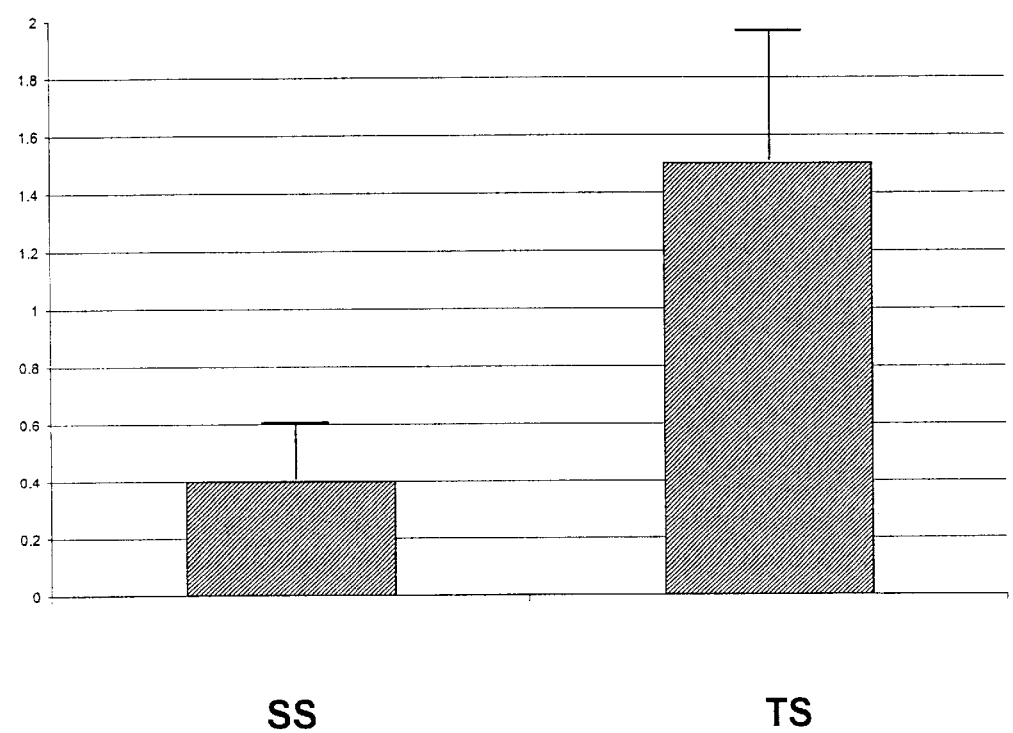

The invention relates to a method for reducing endotoxin levels or removing endotoxins from biological material. The method according to the invention enables, for example, high-purity plasmid DNA to be obtained from natural sources.

The demand for rapid and efficient methods for obtaining high-purity plasmid DNA from biological sources is constantly increasing owing to the increasing importance of recombinant DNA for exogenous expression or therapeutic applications. In particular, the demand for purification methods which can also be carried out on a larger scale is also increasing.

Virtually all known methods for the purification of, in particular, relatively large amounts of plasmid DNA include a chromatographic purification step. The efficiency of this step generally also determines the efficiency and effectiveness of the purification.

Plasmids are epigenomic circular DNA molecules having a length of between 4 and 20 kB, which corresponds to a molecular weight of between $2.6 \times 10^6$ and $13.2 \times 10^6$ daltons. Even in their compact form (super coil), plasmid DNA molecules normally have a size of several hundred nm. Owing to these dimensions, they are larger than the pores of most chromatography materials. This in turn causes, inter alia, the poor binding capacities of the separating materials generally used for plasmid DNA.

A further problem in the purification of plasmid DNA is caused by the impurities from which the plasmid DNA is to be separated. These are firstly genomic DNA and RNA. Exactly like plasmid DNA, these molecules have a strongly anionic character and thus a very similar binding behaviour to separating materials.

The removal of endotoxins is at least as complex. Endotoxins are lipopoly-saccharides (LPSs) which are located on the outer membrane of Gram-negative host cells, such as, for example, *Escherichia coli*. During lysis of the cells, LPSs and other membrane constituents are dissolved out in addition to the plasmid DNA. Endotoxins are present in cells in a number of approximately $3.5 \times 10^6$ copies per cell (*Escherichia Coli* and Salmonella Typhimurium Cell. and Mol. Biology, J. L. Ingraham et al. Eds., 1987, ASM) and thus exceed the number of plasmid DNA molecules by a factor of more than $10^4$. For this reason, plasmid DNA obtained from Gram-negative host cells often contains large amounts of endotoxins. However, these substances result in a number of undesired side reactions (Morrison and Ryan, 1987, Ann. Rev. Med. 38, 417–432; Boyle et al. 1998, DNA and Cell Biology, 17, 343–348). If it is intended to employ the plasmid DNA for, for example, gene therapy, it is of extreme importance that, for example, inflammatory or necrotic side reactions due to the impurities do not occur. There is therefore a great demand for effective methods for reducing endotoxin concentrations to the lowest possible levels.

Known methods for reducing endotoxin levels are based on a plurality of purification steps, frequently using silica supports, glass powder or hydroxy-lapatite, and on reverse-phase, affinity, size-exclusion and/or anion-exchange chromatography.

Firstly, the host cells are digested by known methods, such as, for example, alkaline lysis. However, other lysis methods, such as, for example, the use of high pressure, boiling lysis, the use of detergents or digestion by lysozyme, are also known.

The plasmid DNA in the medium obtained in this way, a "cleared lysate", is principally contaminated by relatively small cell constituents, chemicals from the preceding treatment steps, RNA, proteins and endotoxins. The removal of these impurities usually requires a plurality of subsequent purification steps. Purification by means of anion-exchange chromatography has proven particularly advantageous.

However, the dynamic binding capacity of most anion exchangers for plasmid DNA is only about 0.4 mg/ml of separating material. The reason for this low value is that the functional groups are bonded to the support directly or via short spacers and consequently are only available to a limited extent for interactions with the large plasmid DNA molecules.

A further disadvantage of conventional anion-exchange chromatography is that a considerable amount of endotoxins is bound together with the plasmid DNA and cannot be separated off in this way. Plasmid DNA with endotoxin proportions of greater than 500 EU/mg of plasmid DNA is obtained. In order to reduce the endotoxin levels, further purification steps, such as, for example, chromatographic steps (gel filtration) or precipitation with isopropanol, ammonium acetate or polyethylene glycol, are therefore necessary. Purification methods which combine chromatographic methods, such as, for example, anion-exchange chromatography, and additional endotoxin removal steps enable plasmid DNA having an endotoxin content of less than 50 EU/mg of plasmid DNA to be obtained. However, methods of this type are usually complex, time-consuming and of only limited suitability for the purification of relatively large amounts of DNA.

WO 95/21179 describes a method for the reduction of endotoxin levels in which a cleared lysate is firstly pre-incubated with an aqueous salt solution and detergents. This is followed by purification by ion-exchange chromatography, in which the ion-exchange material is washed with a further salt solution, and the plasmid DNA is eluted and subsequently purified further, for example by isopropanol precipitation. This method likewise has the above-mentioned disadvantages.

Instead of a pure anion-exchange chromatography step, WO 99/63076 uses a mixed-mode principle in which from 25 to 90% of an alcohol is added to the washing buffer. This method likewise typically requires a plurality of steps for achieving effective purification.

The object of the present invention was therefore to provide a method for the chromatographic purification of plasmid DNA which firstly gives plasmid DNA having an endotoxin content of less than 50 EU/mg of plasmid DNA without further purification steps and which secondly is also suitable for the purification of large amounts of DNA.

It has been found that plasmid DNA is obtained in very good purity without further precipitation steps if a cleared lysate is pre-incubated with salt-free detergent solution and subsequently purified by means of anion-exchange chromatography on a tentacle support. The method according to the invention is suitable for the purification of small, but in particular also large amounts of plasmid DNA.

In contrast to the disclosure of WO 95/21179, in which the pre-incubation is carried out with a salt-containing detergent solution, it has now been found that the use of a salt-free detergent solution, in particular in combination with subsequent anion-exchange chromatography on tentacle supports, effects very efficient reduction of endotoxin levels.

The present invention therefore relates to a method for the reduction in endotoxin levels in nucleic acids originating from natural, genetic engineering or biotechnological sources, characterised by the following steps:

a) preparation of a medium which contains the nucleic acids to be purified;
b) pre-incubation of the medium from step a) with a salt-free detergent solution;
c) application of the incubation solution from step b) to anion-exchanger material whose functional groups are bonded to tentacles on the surface of the support;
d) washing of the anion exchanger, in which the impurities are washed out by increasing the ion strength and/or by pH changes, i.e. under anion-exchange chromatography conditions;
e) elution of the sample by a further increase in the ion strength and/or by a pH change.

In a preferred embodiment, the biological source to be purified contains plasmid DNA.

In a preferred embodiment of the method, a DEAE or TMAE anion exchanger is used.

In a preferred embodiment, the washing buffer used for step d) comprises from 0 to 20% (v/v) of an organic solvent or solvent mixture, in particular one or more alcohols, preferably C1 to C5 alcohols, particularly preferably ethanol and/or isopropanol.

In a further preferred embodiment, the medium prepared in step a) is obtained from the natural source by digestion methods, such as alkaline lysis, centrifugation, filtration or precipitation.

The medium is typically a cleared lysate.

FIG. 1 shows a comparison of the dynamic binding capacities of a Fractogel® EMD TMAE HiCap tentacle support (TS) with a conventional silica-DEAE support (SS), corresponding to the material used in WO 95/21179.

Separating materials for chromatography consist, as known to the person skilled in the art, of organic or inorganic polymeric mouldings. For the purposes of the invention, the term mouldings is taken to mean porous and non-porous polymeric materials, such as, for example, bead-shaped mouldings, membranes, tubes, hollow-fibre membranes or sponges.

For the purposes of the present invention, tentacle supports are separating materials in which the functional groups are not bonded individually to the support via spacers. Instead, the functional groups of the separating materials employed in accordance with the invention are bonded to monomer units of polymer chains which are polymerised onto a base support. These flexible polymer structures are sometimes referred to as "tentacle-like". Examples of tentacle supports are disclosed in WO 96/22316, WO 97/49754, EP 0 337 144, DE 43 34 359 and WO 95/09695. Base materials and functional groups of the supports can be selected depending on the specific chromatographic objective. Preference is given to tentacle supports made from methacrylate-based copolymers, particular preference being given, for example, to Fractogel® EMD from Merck KGaA, Germany.

Tentacle supports exhibit much greater binding capacities for plasmid DNA than conventional separating materials. Example 1 and FIG. 1 show a comparison of the dynamic binding capacities of a Fractogel® EMD tentacle support with a silica support (as used in WO 95/21179). The binding capacity of the Fractogel® EMD tentacle support is greater than 1 mg of plasmid/ml of support, whereas the silica support only binds 0.4 mg of plasmid/ml of support.

Chromatographic separating materials or sorbents which are employed for the separation or purification of biopolymers have to have high alkali stability in addition to good separation properties. This is due, in particular, to special purification and sterilisation methods to which the sorbents are subjected.

In the so-called clean in place method, for example, the separating material is treated with 1 M sodium hydroxide solution for a period of from 10 minutes to three hours, depending on the column dimensions. In order to prevent microbial contamination, extended storage of the separating materials is carried out in 0.1 M sodium hydroxide solution. Not all separating materials employed for the separation of biopolymers are stable under such conditions.

Base supports for biochromatography, as are also disclosed for the use according to the invention, for example, in EP 0 337 144 or WO 95/09695, are, for example, natural polymers, such as dextran, agarose or cellulose, silica gel or synthetic polymers, such as polystyrene and methacrylates. In particular, separating materials based on silica gel exhibit, as is known, poor alkali stability. However, supports based on methacrylates can also only be subjected to alkali treatment to a limited extent. For the use according to the invention, particular preference is therefore given to separating materials which have high alkali stability. In this way, the separating materials for use in biochromatography can be adequately sterilised and are even suitable for repeated use.

For the method according to the invention, particular preference is therefore given to alkali-stable sorbents prepared by reaction of a tentacle support containing reactive groups of the formula I with a compound of the formula II.

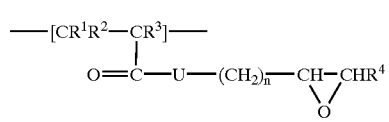

In the formula I:

$R^1$, $R^2$ and $R^3$, independently of one another, are H or $CH_3$, $R^4$ is H, alkyl having 1–5 carbon atoms or aryl having 6–12 carbon atoms, U is —O— or —NH—, and n is an integer between 1 and 5.

In the formula II,

A is $NHR^5$,

B is H, OH, SH or $NHR^5$, where $R^5$ is H, alkyl having 1–5 carbon atoms, preferably H, methyl or ethyl, and m is an integer between 1 and 6, preferably 2 and 3.

The support particularly preferably contains reactive groups of the formula I in which $R^1$ and $R^2$ are H, $R^3$ is $CH_3$, $R^4$ is H, U is —O, and n is 1.

These groups are preferably formed by block or graft polymerisation of glycidyl methacrylate onto a base polymer.

The compound of the formula II used is particularly preferably ethanolamine.

The support very particularly preferably consists of a base polymer comprising polyamide, polyvinyl alcohol or copolymers of (meth)acrylate derivatives and comonomers containing aliphatic hydroxyl groups.

The support may additionally contain groups of the formula III carrying separation effectors.

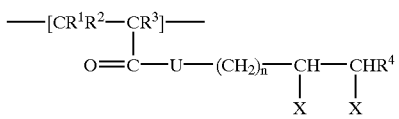

In the formula III:

$R^1, R^2$ and $R^{3,}$ independently of one another, are H or $CH_3$, $R^4$ is H, alkyl having 1–5 carbon atoms or aryl having 6–12 carbon atoms, U is —O— or —NH—, n is an integer between 1 and 5, and one radical X is a separation effector and the other radical X is OH.

The separation effector is, in particular, an ionic group selected from $-NR^7R^8$ and $-N^+R^7R^8R^9$, in which $R^7$ and $R^8$, independently of one another, are H or alkyl having 1–5 carbon atoms, and $R^9$ is alkyl having 1–5 carbon atoms, with the proviso that, if $X = -N^+R^7R^8R^9$, $R^7$ and $R^8$ cannot be H.

The supports containing reactive groups conforming to the formula I are stabilised by reaction with a compound conforming to the formula II. To this end, the support is typically treated with an aqueous 0.5 to 5 M solution of the corresponding compound and mixed by pumping for from 1 to 6 hours at from 20 to 60° C. Particular preference is given to reaction with compounds of the formula II in which m is 1 or 2. Longer-chain compounds increase the hydrophobic character of the moulding.

This subsequent stabilisation step makes the generally base-labile polymers or polymerised-on layers of acrylate derivatives significantly more stable to alkali treatment. An essential disadvantage of the sorbents prepared by block or graft polymerisation with acrylates, which are otherwise distinguished by very good binding capacities, is thus overcome. Preferred functional groups for the use according to the invention are trimethylammoniumethyl (TMAE), diethylaminoethyl (DEAE) or dimethylaminoethyl (DMAE).

In addition to the high binding capacities and the stability of the tentacle supports, it has now been found that they have particular advantages in the purification of plasmid DNA by means of anion-exchange chromatography. The method according to the invention using tentacle supports enables the content of endotoxins to be reduced by from 10- to 20-fold compared with standard methods. Further purification steps, which have to be carried out after the chromatographic purification in the prior art, are therefore generally superfluous in the method according to the invention.

The method according to the invention is particularly suitable for the purification of nucleic acids. These are single-stranded or double-stranded RNA or DNA, RNA/DNA hybrids, DNA fragments, oligonucleotides, amplified DNA or RNA, BACs, or in particular plasmid DNA. The size of the nucleic acids can be between 6 b/bp and 1000 kb/kbp.

The nucleic acids to be purified may originate from any natural, genetic-engineering or biotechnological source, such as, for example, prokaryotic cell cultures. If nucleic acids from cell preparations are to be purified, the cells are firstly digested by known methods, such as, for example, lysis. If the material to be purified has already been pre-treated in another way, lytic digestion is unnecessary. For example, the medium can be obtained from biological material by removal of the cell debris and a precipitate of RNA, from nucleic acid samples which have already been pre-purified and, for example, are present in buffer, or alternatively from nucleic acid solutions which have been formed after amplification and still contain endotoxin impurities. Filtration, precipitation or centrifugation steps may be necessary. The person skilled in the art is able to select a suitable digestion method depending on the source of the biological material. In any case, the sample to be purified should, for the method according to the invention, be present in a medium which does not form precipitates or cause other undesired side reactions on addition of the detergent solution. The medium is preferably a lysate obtained from cells, such as, for example, a cleared lysate.

For the purification of plasmid DNA from *E. coli,* the cells are, for example, firstly lysed by alkaline lysis with NaOH/SDS solution. Addition of an acidic potassium-containing neutralisation buffer then causes the formation of a precipitate, which can be removed by centrifugation or filtration. The clear supernatant remaining, the cleared lysate, can be employed as starting material, i.e. as medium, for the method according to the invention. It is also possible firstly to concentrate or pre-purify the cleared lysate by known methods, such as dialysis or precipitation.

In the first step of the method according to the invention, a salt-free, nonionic detergent solution is added to the cleared lysate. If salts enter the solution through impurities in the detergents, their concentration should be less than 0.005%, i.e. less than 1 mM. The detergents employed are nonionic detergents, such as, for example, Triton® X-100, Triton® X-114, Tween® 20 or Igepal® CA 630, or mixtures thereof. After addition to the sample, the detergents are preferably present in final concentrations of between 0.01 and 30% (v/v), particularly preferably between 0.5 and 15% (v/v).

After the pre-incubation, the lysate is added to an anion exchanger which is suitable in accordance with the invention. Charging, washing and elution are carried out by known methods. The extent and strength of the binding of a target molecule to the ion exchanger depends, inter alia, on the pH and ion strength of the buffer, the isoelectric point of the target molecule and the density of the charges on the matrix. In general, the sample is charged onto a column equilibrated with a buffer of low ion strength, after which unbound molecules are washed out. By increasing the ion strength and/or changing the pH, impurities are washed out selectively before the target molecules are eluted through a further increase in the ion strength and/or a further change in the pH.

The person skilled in the art is able to select suitable reagents for the particular tentacle support or the biological material to be purified. It should be noted here that the interaction between the plasmid DNA and the anion exchange group of a, for example, Fractogel® EMD TMAE support is influenced more strongly by differences in the ion strength than is the case on use of conventional supports, for example silica-DEAE supports. Although the pK of TMAE, at above 13, is greater than that of DEAE, at 11, special charging conditions must therefore be observed on use of Fractogel® EMD tentacle supports. In particular, it must be ensured that the ion strength of the sample with which the support is to be charged is sufficiently well below that of the elution point of the plasmid DNA.

It has been found, for example, that the use of isopropanol-containing buffers instead of ethanol-containing buffers is advantageous. As proposed in DE 44 03 693, particularly good transfection rates (or lower endotoxin impurity levels) of the nucleic acids prepared can be achieved through the use of isopropanol-containing buffers. The washing and elution buffers employed in accordance with the invention should not contain more than 20% (v/v) of one or more organic solvents in order that the washing-out of the impurities and also the elution of the nucleic acids takes place by anion-exchange chromatography, i.e. in particular depending on the ion strength and/or on pH changes, and further washing steps are unnecessary. In particular, the organic solvents employed are C1- to C5-alcohols, preferably ethanol and/or isopropanol. The buffers particularly preferably comprise between 10 and 15% of ethanol and/or isopropanol.

The method according to the invention thus typically comprises the following steps:
   incubation of the medium comprising the nucleic acids (typically the cleared lysate) with a salt-free detergent solution (duration about 15–30 min)
   application of the incubation solution to the pre-calibrated anion exchanger column
   washing of the column with a washing buffer
   elution of the plasmid DNA with an elution buffer.

After elution from the anion exchanger, the plasmid DNA purified by the method according to the invention has an endotoxin content of less than 50 EU/mg of plasmid, in most cases even an endotoxin content of less than 25 EU/mg of plasmid. In conventional methods, these values are only achieved through additional purification steps, such as precipitation or gel filtration.

The method according to the invention, which combines salt-free pre-incubation with a chromatography step on a specific anion exchanger, is thus from 5 to 10 times more efficient than other methods, which use, for example, a salt-containing detergent solution for the pre-incubation. If the pre-incubation of the method according to the invention is carried out with a salt-containing detergent solution, the efficiency of the purification drops. Accordingly, an increase in the ion strength during the pre-incubation on use of tentacle supports, such as, for example, Fractogel® EMD anion exchangers, results in an increase in the endotoxin content of the eluted sample.

The eluted nucleic acids can be combined or collected in fractions and sent to their further use. Since the purified samples after elution from the anion exchanger are usually contaminated by the salts of the elution buffer, it may be necessary, in order to remove the salts, to carry out additional purification of the sample, for example by dialysis or alcohol precipitation. However, these steps in the method according to the invention only serve to remove salts, not, as in the prior art, further to reduce endotoxin levels.

Besides the quality of the purified nucleic acids, the scale on which the nucleic acids can be purified is also of crucial importance. The method according to the invention is suitable both for the purification of small amounts (less than 1 mg) and for the purification of large amounts (from 1 mg to several 100 g or more).

Even without further details, it is assumed that a person skilled in the art will be able to utilise the above description in its broadest scope. The preferred embodiments and examples should therefore be regarded merely as descriptive disclosure which is absolutely not limiting in any way.

The complete disclosure content of all applications, patents and publications mentioned above and below is incorporated into this application by way of reference.

EXAMPLES

The following solutions were used for the purifications:
1. CL resuspension buffer
   50 mM TRIS.HCl, pH 8.0
   10 mM EDTA
   100 µg/ml DNAse-free ribonuclease A
2. CL lyse buffer
   200 mM NaOH
   1% (w/v) SDS (sodium dodecyl sulfate)
3. CL neutralisation buffer
   3.0 M KOAc (potassium acetate), pH 5.5
4. IE equilibration buffer
   50 mM TRIS, pH 6.5
   500 mM NaCl
   15% (v/v) ethanol
5. IE washing buffer
   50 mM TRIS, pH 6.5
   625 mM NaCl
   15% (v/v) ethanol
6. IE elution buffer
   50 mM TRIS, pH 8.5
   1500 mM NaCl
   15% (v/v) ethanol The bacteria cultures were cultivated by known methods and processed to give a cleared lysate. This is therefore only explained briefly below:
1. Cells from a 50 ml to 3 l bacteria culture were centrifuged at 6000 g for 15 minutes and resuspended in 4 ml of CL resuspension buffer per 50 ml of culture. A cloudy suspension is obtained which is free from relatively large cell agglomerates.
2. The same volume of CL lyse buffer is added, and the components are mixed (inversion/swirling) until the solution is clear. This solution must not be stored for longer than 10 minutes at room temperature.
3. The same volume of CL neutralisation buffer (4 ml per 50 ml of culture) is then added, and the solution is mixed until the lysate becomes cloudy and flocculates out. The lysate is subsequently incubated on ice for 15–20 minutes.
4. The solution is then centrifuged at greater than 20,000 g for 30 minutes at 4° C. to give a cleared lysate.
5. The supernatant of the cleared lysate is transferred into a new container.

Example 1

Comparison of the Binding Capacities

The dynamic binding capacities of a Fractogel® EMD TMAE tentacle support (TS) were compared with a conventional silica support (SS) from Qiagen with grafted-on functional groups.

Bacteria (overnight cultures DH5α transformed with pTriEx plasmid, JM109 transformed with pBluescipt plasmid and NovaBlue transformed with pTriEx plasmid) were pelleted and resuspended, lysed and neutralised successively with CL resuspension, lyse and neutralisation buffer. The cell debris of the various lysates was centrifuged off. At this point, the various cleared lysates were each divided into two fractions in order to ensure that identical starting material was used for the purifications.

One of the two fractions of each cleared lysate (all with saturating amount of plasmid relative to the amount of support) was charged onto the Fractogel® support and the other was charged onto the silica support.

Before charging with the samples, the Fractogel® EMD TMAE HiCap columns were equilibrated with 5 column volumes of IE equilibration buffer. For anion-exchange chromatography with the silica support QIAGEN® Plasmid Maxi Kit, Cat No. 12163, the buffers mentioned in WO 95/21179, Example 1, were used. During charging of the columns, all eluates were collected in fractions and analysed for their plasmid content.

FIG. 1 shows the result of the analysis. The results of 4 independent experiments were calculated. The dynamic binding capacity is indicated on the ordinate in mg of plasmid DNA/ml of support. It is found that the Fractogel® EMD TMAE support has a significantly higher binding capacity for plasmid DNA.

Example 2

Purification of pBacMam DNA

Bacteria (an overnight culture of DH5α cells transformed with a pBacMam plasmid) were pelleted and resuspended, lysed and neutralised successively with CL resuspension, lyse and neutralisation buffer. The cell debris was centrifuged off.

At this point, the cleared lysate was divided into various fractions in order to ensure that identical starting material is used for all purifications.

The following fractions were formed:

(a) The cleared lysate is not pre-incubated, but instead charged directly onto the Fractogel® support.

(b) The cleared lysate is pre-incubated for 30 minutes with 1/10 of its volume of a salt-free 20% Triton® X-114 solution and then charged onto the Fractogel® support.

(c) The cleared lysate is subjected to 2 or 3 successive phase separations with uncondensed Triton® X-114 detergent solution by known methods (Manthorpe et al. (1993), Hum. Gene Ther. 4,419–431) and then charged onto the Fractogel® support.

Before charging with the samples, the Fractogel® EMD TMAE HiCap columns were equilibrated with 5 column volumes of IE equilibration buffer. After charging, the columns were washed with 10 column volumes of IE washing buffer and eluted with 4 column volumes of IE elution buffer. The eluate was analysed, without further purification steps, by the LAL (limulus amoebocyte lysate) test (Bayston and Cohen (1990), J. Med. Microbiol. 31, 73–83). The test was carried out as described in the European Pharmaco-poeia, 3rd Edition (1997), Chapter 2.6.14 and in accordance with the FDA "Guideline on validation of the LAL Test as an endproduct endotoxin test for human and animal parenteral drugs, biological products and medical devices" of December 1987. The lysate sensitivity was below 0.12 EU/ml.

Table 1 shows the endotoxin values obtained from three independent experiments:

TABLE 1

| | Without pre-incubation | Incubation with salt-free detergent solution | Triton ® X-114 phase separation |
|---|---|---|---|
| | Endotoxin contamination in E.U./mg of pBacMam | | |
| 1 | 116.36 | 7.27 | 8.00 |
| 2 | 53.30 | 5.10 | 6.30 |
| 3 | 147.70 | 5.30 | 4.00 |
| Average | 105.79 ± 39.26 | 5.89 ± 0.98 | 6.10 ± 1.64 |

Two successive Triton® X-114 detergent phase separations were carried out in Experiment 2, and three were carried out in each of Experiments 1 and 3.

By combining pre-incubation with salt-free detergent solution with anion-exchange chromatography on a Fractogel® EMD anion exchanger, endotoxin values of <25 EU/mg of plasmid DNA are obtained. Without the further purification steps, such as precipitation or gel filtration, the DNA contains just as small an amount of endotoxins as after very much more complex detergent phase separation.

Example 3

Purification of pTriEx DNA Using Various Nonionic Detergents

Bacteria (an overnight culture of DH5α cells transformed with a pTriEx plasmid) were pelleted and resuspended, lysed and neutralised successively with CL resuspension, lyse and neutralisation buffer. The cell debris was centrifuged off. At this point, the cleared lysate was divided into various fractions in order to ensure that identical starting material is used for all purifications.

The following fractions were formed:

(a) The cleared lysate is not pre-incubated, but instead charged directly onto the Fractogel® support.

(b) The cleared lysate is pre-incubated for 60 minutes on ice with 1/10 of its volume of various salt-free 20% detergent solution and then charged onto the Fractogel® support.

Before charging with the samples, the Fractogel® EMD TMAE HiCap columns were equilibrated with 5 column volumes of IE equilibration buffer. After charging, the columns were washed with 10 column volumes of IE washing buffer and eluted with 4 column volumes of IE elution buffer. The eluate was analysed, without further purification steps, by the turbidimetric LAL test. The results are shown in Table 2:

TABLE 2

| | Salt-free detergent solution | Endotoxin contamination in E.U./mg of pTriEx |
|---|---|---|
| 1 | no pre-incubation | 116.36 |
| 2 | Triton ® X-100 | 12.63 |
| 3 | Triton ® X-114 | 3.58 |
| 4 | Igepal ® CA 630 | 4 |
| 5 | Tween ® 20 | 14.55 |

It is found that pre-incubation with salt-free detergent solution results in a significant reduction in the endotoxin content.

Example 4

Purification of pTriEx DNA with Salt-free and Salt-containing Igepal® Detergent Solutions on Fractogel® EMD TMAE HiCap and QIAGEN® Supports The cleared lysate was prepared as described in Example 3, but starting from an overnight culture of NovaBlue cells transformed with a pTriEx plasmid.

The cleared lysate is divided into various fractions in order to ensure that identical starting material is used for all purifications.

(a) 2 fractions were not pre-incubated, but instead applied directly to the two supports (Fractogel® EMD TMAE HiCap and QIAGEN®-DEAE).

(b) 2 fractions were pre-incubated with a salt-containing detergent solution and then applied to the supports. The pre-incubation was carried out as described in WO 95/21179, Example 1.

(c) 2 fractions were pre-incubated with salt-free detergent solution as described in Example 3 and then applied to the supports.

For anion-exchange chromatography on the Qiagen support, the buffers mentioned in WO 95/21179, Example 1, were used. Since the elution points of the plasmid DNA are different for the two separating materials, however, the buffers cannot have a completely identical composition. For the Fractogel® EMD TMAE HiCap support, the buffers mentioned at the beginning of the examples were used.

The eluates from the ion-exchange columns were collected and analysed directly, without further purification steps, by the LAL test for their endotoxin content.

The results are shown in Tables 3 and 4:

TABLE 3

| | Amount applied | |
|---|---|---|
| | 2211.84 EU total Eluate Fractogel ® | 2211.84 EU total Eluate QIAGEN ® |
| No pre-incubation | 330.7 EU/mg | 981.5 EU/mg |
| Pre-incubation with salt-free detergent solution | 19.5 EU/mg | 458.2 EU/mg |
| Pre-incubation with salt-containing detergent solution | 83.2 EU/mg | 924.6 EU/mg |

The following improvements compared with ion-exchange chromatography without pre-incubation (standard IEC) thus arise with the two supports and pre-incubation (with and without salt):

TABLE 4

| | Fractogel ® | | QIAGEN ® | |
|---|---|---|---|---|
| | Total | Improvement compared with Standard IEC | Total | Improvement compared with Standard IEC |
| No pre-incubation | 307.2 EU | / | 921.6 EU | / |
| Pre-incubation with salt/detergent | 76.8 EU | 4-fold | 921.6 EU | none |
| Pre-incubation with detergent | 19.2 EU | 16-fold | 460.8 EU | 2-fold (not significant) |

The table shows the means of two independent experiments. It is found that the combination of pre-incubation with salt-free detergent solution/Fractogel® support produces by far the best purification.

What is claimed is:

1. Method for the reduction in endotoxin levels in nucleic acids originating from natural, genetic engineering or biotechnological sources, comprising the following steps:
   a) preparation of a medium which contains the nucleic acids to be purified;
   b) pre-incubation of the medium from step a) with a salt-free detergent solution;
   c) application of the incubation solution from step b) to anion-exchanger material whose functional groups are bonded to tentacles on the surface of the support;
   d) washing of the anion exchanger, in which the impurities are washed out by increasing the ion strength and/or by pH changes;
   e) elution of the sample by a further increase in the ion strength and/or by a pH change.

2. Method for reducing endotoxin levels according to claim 1, wherein the biological source to be purified contains plasmid DNA.

3. Method according to claim 1, wherein the anion exchanger contains DEAE or TMAE as functional groups.

4. Method according to claim 1, wherein the medium prepared in step a) has been obtained from a natural source by a digestion method.

5. A method according to claim 4, wherein the digestion method is alkaline lysis, centrifugation, filtration or precipitation.

6. A method according to claim 1, wherein the medium which contains the nucleic acids to be purified contains single-stranded or double-stranded RNA or DNA, RNA/DNA hybrids, DNA fragments, oligonucleotides, amplified DNA or RNA, BACs, or plasmid DNA.

7. A method according to claim 1, wherein the anion exchanger is washed by a buffer that contains an organic solvent or solvent mixture up to 20% by volume.

8. A method according to claim 7, wherein the solvent is or the solvent mixture comprises ethanol or methanol or both ethanol and methanol.

9. A method according so claim 1, wherein the medium is a cleared lysate.

10. A method according to claim 1, wherein the functional groups of the anion-exchanger material are bonded to monomer units of polymer chains which are polymerised onto a base support.

11. A method according to claim 1, wherein the tentacles are copolymers that comprise methacrylate.

12. A method according to claim 1, wherein the anion-exchanger material are prepared by reacting a tentacle support containing reactive groups of formula I with a compound of formula II,

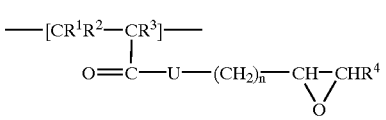

wherein $R^1, R^2$ and $R^3$, independently of one another, are H or $CH_3$, $R^4$ is H, alkyl having 1–5 carbon atoms or aryl having 6–12 carbon atoms, U is —O— or —NH—, and n is an integer of 1 to 5, $$A\text{—}(CH_2)_m\text{—}B \qquad II$$

wherein
- A is $NHR^5$,
- B is H, OH, SH or $NHR^5$,
- $R^5$ is H, alkyl having 1–5 carbon atoms, and
- M is an integer of 1 to 6.

13. A method according to claim 12, wherein
- $R^1$ and $R^2$ are H,
- $R^3$ is $CH_3$,
- $R_4$ is H,
- U is —O, and
- n is 1.

14. A method according to claim 12, wherein
- $R^5$ is H, methyl or ethyl, and
- m is an integer of 2 to 3.

15. A method according to claim 12, wherein the compound of formula II is ethanol amine.

16. A method according to claim 1, wherein the support contains a base polymer which comprises polyamide, polyvinyl alcohol or copolymers of (meth)acrylate derivatives or comonomers containing aliphatic hydroxyl groups, and optionally contains groups of formula III,

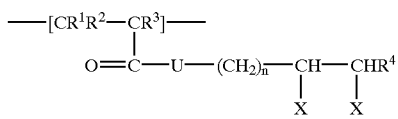

III wherein
- $R^1, R^2$ and $R^3$, independently of one another, are H or $CH_3$,
- $R^4$ is H, alkyl having 1–5 carbon atoms or aryl having 6–12 carbon atoms,
- U is —O— or —NH—,
- n is an integer of 1 to 5, and
- one radical X is OH, and the other X is —$NR^7R^8$ or —$N^+R^7R^8R^9$, in which
- $R^7$ and $R^8$, independently of one another, are H or alkyl having 1–5 carbon atoms, and
- $R^9$ is alkyl having 1–5 carbon atoms,
- with the proviso that, if X is —$N^+R^7R^8R^9$, then $R^7$ and $R^8$ are not H.

17. A method according to claim 1, wherein the anion exchanger contains DMAE as functional groups.

18. A method according to claim 1. wherein the salt-free detergent solution contains less than 1 mM salt and is present in the medium in 0.01 to 30% by volume.

19. A method according to claim 1, wherein the medium which contains the nucleic acids to be purified contains plasmid DNA.

20. A method according to claim 7, wherein the buffer contains 10 to 15% of ethanol and/or isopropanol.

* * * * *

UNITED STATES PATENT AND TRADEMARK OFFICE
CERTIFICATE OF CORRECTION

PATENT NO. : 6,617,443 B2
DATED : September 9, 2003
INVENTOR(S) : Robertus Hendriks et al.

It is certified that error appears in the above-identified patent and that said Letters Patent is hereby corrected as shown below:

Column 12,
Line 41, reads "so" should read -- to --

Column 13,
Line 7, reads "M is" should read -- m is --

Column 14,
Line 23, reads "claim 1." should read -- claim 1, --

Signed and Sealed this

Eighth Day of March, 2005

JON W. DUDAS
*Director of the United States Patent and Trademark Office*